(12) United States Patent
Niwa et al.

(10) Patent No.: US 7,347,816 B2
(45) Date of Patent: Mar. 25, 2008

(54) ADAPTOR FOR ENDOSCOPE FORCEPS OPENING

(75) Inventors: Hiroshi Niwa, Koganei (JP); Chieko Aizawa, Hachioji (JP); Fumiyuki Onoda, Tama (JP)

(73) Assignee: Olympus Corporation, Tokyo (JP)

( * ) Notice: Subject to any disclaimer, the term of this patent is extended or adjusted under 35 U.S.C. 154(b) by 545 days.

(21) Appl. No.: 10/951,461

(22) Filed: Sep. 28, 2004

(65) Prior Publication Data

US 2005/0070757 A1    Mar. 31, 2005

(30) Foreign Application Priority Data

Sep. 30, 2003 (JP) ............... 2003-342420
Mar. 25, 2004 (JP) ............... 2004-090015

(51) Int. Cl.
*A61B 1/00* (2006.01)
(52) U.S. Cl. ............. 600/154; 600/102; 600/104; 600/159; 604/167
(58) Field of Classification Search ........... 600/102, 600/104, 106, 154, 159; 604/167
See application file for complete search history.

(56) References Cited

U.S. PATENT DOCUMENTS

| 4,240,411 | A | * | 12/1980 | Hosono ............ 600/154 |
| 4,920,953 | A | * | 5/1990 | McGown ............ 600/154 |
| 6,117,070 | A | | 9/2000 | Akiba |
| 6,165,124 | A | * | 12/2000 | Ouchi ............ 600/154 |
| 6,254,529 | B1 | * | 7/2001 | Ouchi ............ 600/154 |
| 6,315,774 | B1 | * | 11/2001 | Daniel et al. ............ 606/15 |
| 2003/0028096 | A1 | | 2/2003 | Niwa et al. |
| 2004/0006356 | A1 | * | 1/2004 | Smith ............ 606/167 |
| 2004/0015050 | A1 | * | 1/2004 | Goto et al. ............ 600/104 |

FOREIGN PATENT DOCUMENTS

JP    2003-38427    2/2003

* cited by examiner

*Primary Examiner*—Linda C. M. Dvorak
*Assistant Examiner*—Matthew J. Kasztejna
(74) *Attorney, Agent, or Firm*—Scully, Scott, Murphy & Presser, P.C.

(57) ABSTRACT

In an adaptor for endoscope forceps opening: an adaptor connecting member includes an opening groove which is formed in its axial direction and from/to which the treatment tool is detached/attached, and an engaging groove integrally-formed to the opening groove; a treatment tool integrating member includes a flexible long member connected to the adaptor connecting member and an engaging projection which is fit into the engaging groove and fixes the treatment tool in close contact thereat; and a treatment tool position changing member is rotatably connected to the adaptor connecting member and includes a through-groove from which the treatment tool is detached and an opening notch portion communicated with the through-groove, wherein the opening groove, engaging groove, through-groove, and opening notch portion are arranged on the straight line.

8 Claims, 11 Drawing Sheets

ADAPTOR FOR ENDOSCOPE FORCEPS OPENING

This application claims benefit of Japanese Application No. 2003-342420 filed on Sep. 30, 2003 and No. 2004-90015 filed on Mar. 25, 2004, the contents of which are incorporated by this reference.

BACKGROUND OF THE INVENTION

1. Field of the Invention

The present invention relates to an adaptor for endoscope forceps opening, and more particularly, to an adaptor for endoscope forceps opening which is attached to an endoscope forceps opening and regulates the movement of a treatment tool or the like.

2. Description of the Related Art

Recently, an endoscope is widely used in the medical field and the industrial field. Particularly, in the endoscope used in the medical field, a soft inserting portion is inserted to the body cavity from the oral cavity or anus. With the above-mentioned endoscope, the organ at the deep portion in the body cavity is observed or diagnosed without the incision of the body surface, or the treatment and curing such as the removal of the lesion organ in the body cavity or the resection of the polyp are performed by inserting a treatment tool in a treatment tool inserting channel (hereinafter, referred to as a treatment tool channel) which is arranged to the endoscope if necessary.

Recently, in one of the foregoing endoscopes, a probe for detecting the endoscope shape (hereinafter, referred to as a shape detecting probe) is inserted in the treatment tool channel and simultaneously the inserting portion of the endoscope is inserted in the body cavity. Then, the shape of the inserting portion upon inserting the endoscope is displayed on a screen of an endoscope shape observing device which is arranged in accordance with the shape detecting probe. In the above-mentioned endoscope, the inserting operability is improved by smoothly performing the operation on the hand side, such as the operation for bending a bending portion arranged to the inserting portion while checking the shape of inserting portion of the endoscope.

However, while the treatment tool projected from the treatment tool channel faces the lesion organ which is removed during the use of the endoscope, an operator operates the endoscope and the treatment tool on his hand side, and he/she must execute the complicated operation such as the adjustment of the projecting amount of the treatment tool or removal of the lesion organ. The above operation takes a long time for smoothly executing the operation.

The shape detecting probe is inserted to a predetermined position of the treatment tool channel and the endoscope inserting portion is further inserted to a target portion in the body cavity, and then the twisting operation of the inserting portion is performed or the bending portion is bent. In this case, if the shape detecting probe is not held to the treatment tool channel, the shape detecting probe is projected from the distal surface of the endoscope.

Normally, the distal portion of the shape detecting probe is previously arranged at the position near the hand side by a predetermined amount from the predetermined position in the treatment tool channel, and the endoscope is inserted.

However, when the shape detecting probe is not held to the treatment tool channel, the shape detecting probe is moved with respect to the treatment tool channel. Therefore, the shape of the inserting portion is not detected with high precision.

Conventional adaptors for endoscope forceps opening are suggested to hold the shape detecting probe to the treatment tool channel at the predetermined position thereof and to regulate the movement of the treatment tool so as to detect the shape of the inserting portion with the high precision. For example, Japanese Unexamined Patent Application Publication No. 2003-38427 suggests one of the conventional adaptors for endoscope forceps opening.

As disclosed in Japanese Unexamined Patent Application Publication No. 2003-38427, the adaptor for endoscope forceps opening comprises: an adaptor connecting member which is detachable to an endoscope forceps opening which is communicated with the treatment tool channel in which the treatment tool is inserted; a treatment tool integrating member which is fixed in close contact at a part of the treatment tool projected from the endoscope forceps opening; a pressing member which fixes in close contact at the treatment tool integrating member to the part of the treatment tool by pressing the treatment tool integrating member with a predetermined force and by thus elastically modifying the treatment tool integrating tool; and a treatment tool position changing member which stepwise changes the inserting position of the treatment tool with which the treatment tool integrating member is in close contact, together with the treatment tool integrating member.

Accordingly, the treatment tool or the like, which is inserted in the treatment tool inserting channel and is arranged at the predetermined position, is certainly positioned. Further, the position of the treatment tool is stepwise changed if necessary.

SUMMARY OF THE INVENTION

According to the present invention, an adaptor for endoscope forceps opening comprises: an adaptor connecting member which is detachably arranged to a forceps valve of an endoscope forceps opening communicated with a treatment tool inserting channel for inserting a treatment tool; a treatment tool integrating member which is fixed in close contact at a part of the treatment tool projected from the forceps valve; and a treatment tool position changing member which stepwise changes the inserting position of the treatment tool in the treatment tool inserting channel when the treatment tool integrating member is in close contact at the treatment tool. In the adaptor for endoscope forceps opening, the adaptor connecting member comprises an opening groove which is formed in its axial direction and from/to which the treatment tool is detached/attached, and an engaging groove which is integrally formed to the opening groove, the treatment tool integrating member comprises a flexible long member which is connected to the adaptor connecting member and an engaging projection which is fit into the engaging groove and fixes the treatment tool in close contact therewith, the treatment tool position changing member is rotatably connected to the adaptor connecting member and comprises a through-groove from which the treatment tool is detached and an opening notch portion communicated with the through-groove, and the opening groove, the engaging groove, the through-groove, and the opening notch portion are arranged substantially on the straight line.

Other features and advantages of the present invention will be obvious by the following description.

DESCRIPTION OF THE PREFERRED EMBODIMENTS

Figure 1:
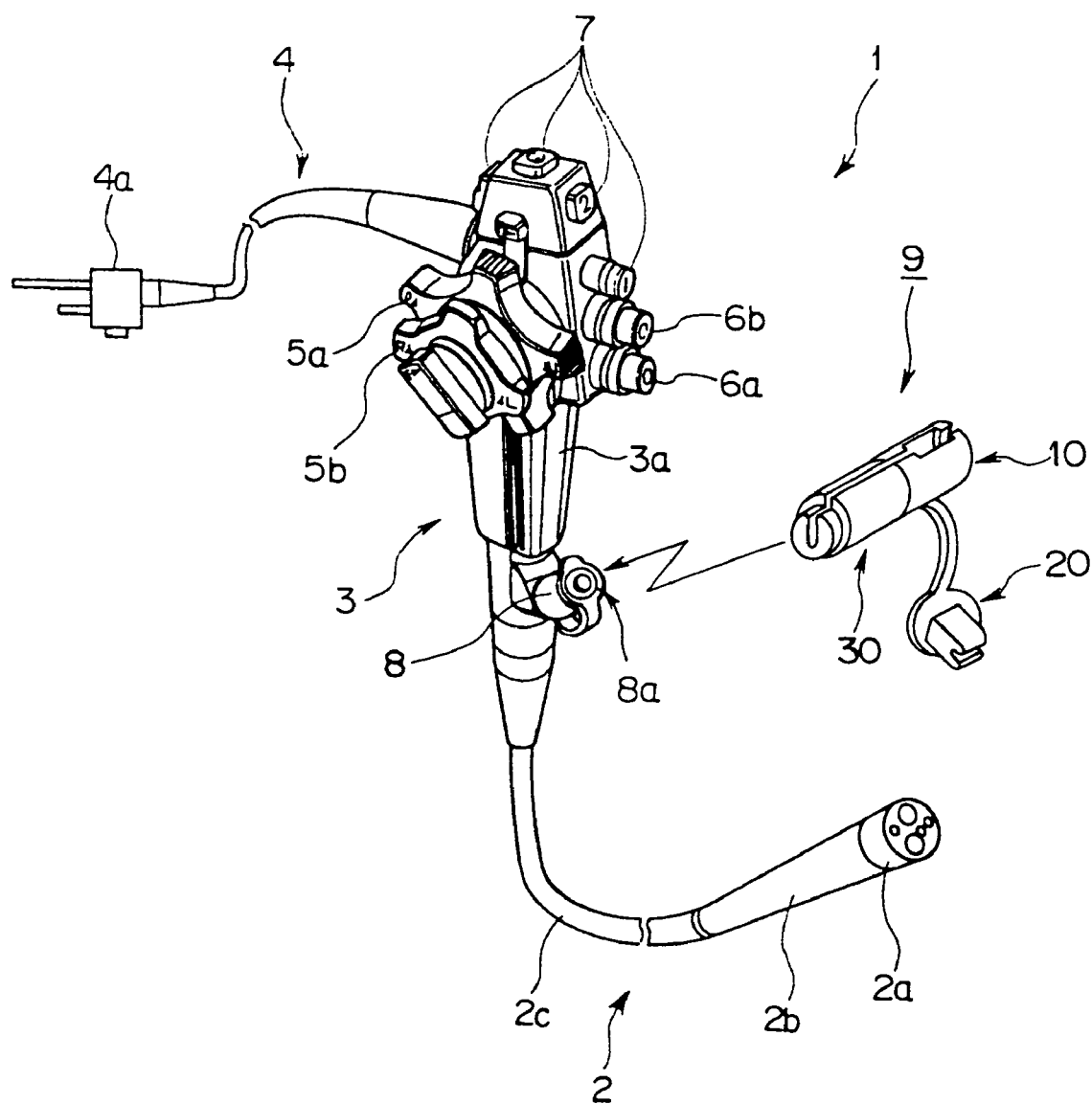
FIG. 1 is a diagram showing the structure of an adaptor for endoscope forceps opening and an endoscope using it according to the first embodiment of the present invention.
Figure 2:
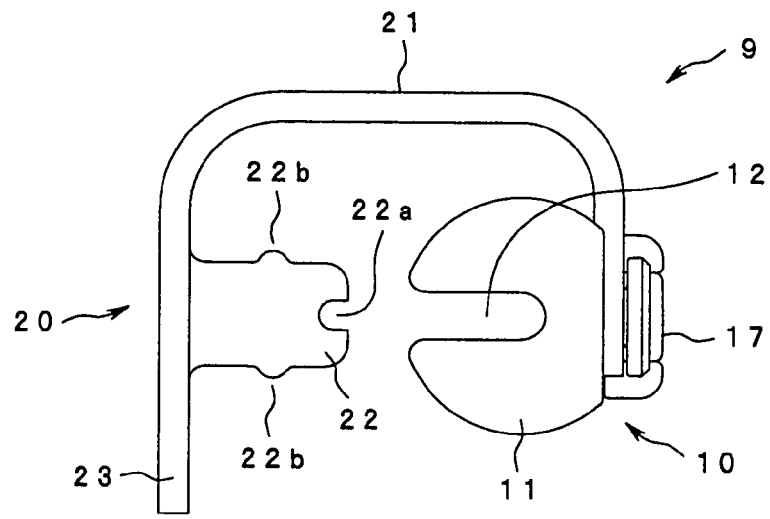
FIG. 2 is a top plan view of three plan views showing the structure of the adaptor for endoscope forceps opening shown in FIG. 1.
Figure 3:
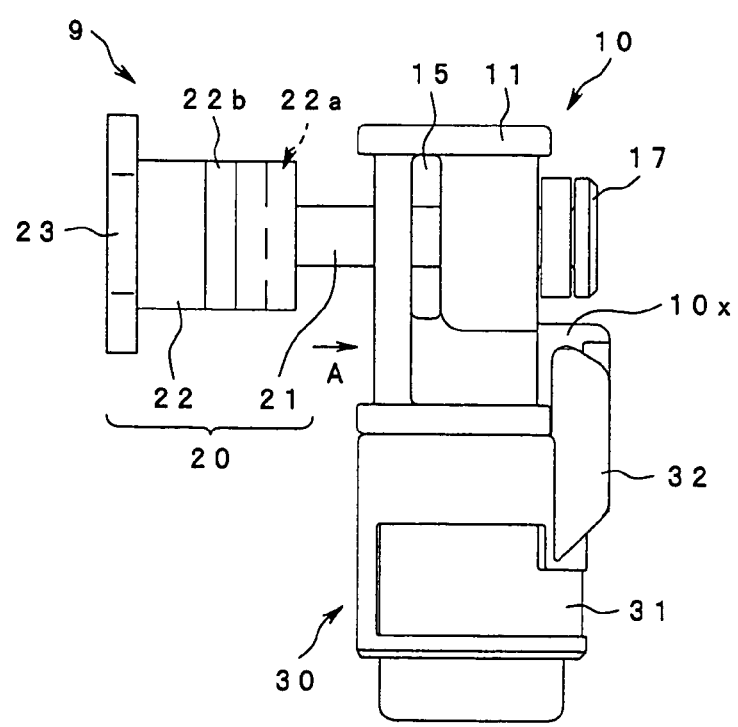
FIG. 3 is a front plan view of the three plan views showing the structure of the adaptor for endoscope forceps opening shown in FIG. 1.
Figure 4:
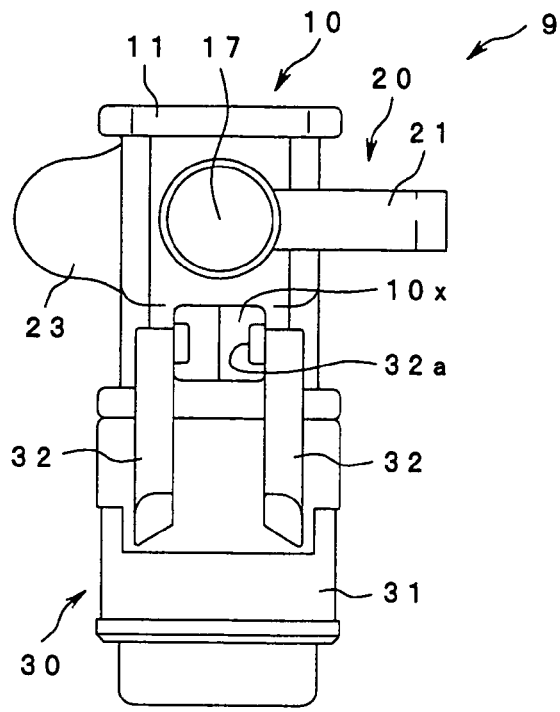
FIG. 4 is a right side view of the three plan views showing the structure of the adaptor for endoscope forceps opening shown in FIG. 1.

First, a description is given of an endoscope 1 using an adaptor 9 for endoscope forceps opening according to the first embodiment of the present invention with reference to FIG. 1.

Referring to FIG. 1, according to the first embodiment, the endoscope 1 using the adaptor 9 for endoscope forceps opening mainly comprises: a long and thin inserting portion 2, which can be inserted in the body cavity; an operating portion 3 which is arranged at the base end portion of the inserting portion 2 and is gripped by an operator; and a universal cord 4 which has an inserted signal cable and light guide fiber (which are not shown) extended from one side portion of the operating portion 3 and has an endoscope connector 4a at one end portion thereof.

The inserting portion 2 comprises, starting from the distal side: a hard distal portion 2a; a bending portion 2b having a plurality of bending pieces that are continuously in contact with each other, which is bent in the up, down, left, and right directions; and a soft flexible tube 2c, which are continuously arranged.

The operating portion 3 comprises: bending portion operating knobs 5a and 5b which bend the bending portion 2b in the up and down directions and in the left and right directions; an air/water feed operating button 6a; a suction operating button 6b; and various control switches 7, and the like, which control an external device (not shown).

The operating portion 3 further comprises a grip portion 3a for gripping the endoscope 1 by the operator, containing a hard resin member such as polysulfone. Projected at one side portion of the grip portion 3a is an adaptor forceps opening (hereinafter, abbreviated to a forceps opening) 8 of a treatment tool inserting channel (hereinafter, referred to as a treatment tool channel) for inserting treatment tools such as forceps and a shape detecting probe (hereinafter, simply referred to as a treatment tool). Attached to the forceps opening 8 is a forceps valve 8a containing an elastic member such as silicon rubber or the like. An adaptor 9 for endoscope forceps opening (hereinafter, abbreviated to an adaptor 9) is arranged to the forceps valve 8a.

The adaptor 9 holds the treatment tool or the like to the treatment tool channel at a predetermined position thereof, and is a member for regulating the movement of the treatment tool. The adaptor 9 mainly comprises an adaptor connecting member 10, a treatment tool integrating member 20, and a treatment tool position changing member 30. The adaptor connecting member 10, the treatment tool integrating member 20, and the treatment tool position changing member 30 are integrally and continuously set.

Hereinbelow, a description is given of the detailed structure of the adaptor 9 with reference to FIGS. 2 to 7.

The adaptor 9 is formed by integrating the adaptor connecting member 10, the treatment tool integrating member 20, and the treatment tool position changing member 30, as mentioned above.

Figure 5:
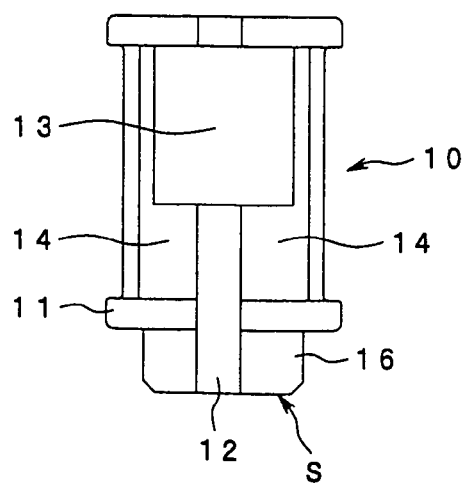
FIG. 5 is a plan view showing only an adaptor connecting member among components in the adaptor for endoscope forceps opening shown in FIG. 1, viewing in a direction shown by an arrow A shown in FIG. 3.

Referring to FIG. 5, the adaptor connecting member 10 comprises: a tube member 11 mainly containing a resin member; an opening groove 12 which is formed in the same direction as the axial direction of a treatment tool or the like 50 (hereinafter, referred to as a treatment tool 50, not shown in FIGS. 2 to 5, refer to FIGS. 6 and 7) which is inserted/detached in/from the tube member 11; an engaging groove 13 which is integrally formed to the opening groove 12; and a supporting-axis inserting hole 10a for coaxially and rotatably supporting the treatment tool position changing member 30. The adaptor connecting member 10 is detachably arranged to the forceps valve 8a, which is communicated with the treatment tool channel in which the treatment tool 50 is inserted, of the forceps opening 8 in the endoscope 1.

Specifically, the adaptor connecting member 10 has the opening groove 12 in the axial direction in the center of the tube member 11 mainly containing a resin member. The treatment tool 50 is easily inserted or pulled-out into/from the opening groove 12. The engaging groove 13 is integrally arranged to the opening groove 12. An attaching base 14 is planarity formed around the opening of the engaging groove 13.

The engaging groove 13 has, at a predetermined depth position thereof, an engaging hole 15 (refer to FIGS. 3 and 6) which is formed like a slit with a predetermined dimension in the direction perpendicular to the depth direction of the engaging groove 13. As will be described later with reference to FIG. 6, the engaging hole 15 has a function for preventing the easy pull-out of the adaptor connecting member 10 and the treatment tool integrating member 20 and for keeping the engaging state thereof by fitting a boss 22b of an engaging projection 22 on the treatment tool integrating member 20 into the engaging hole 15, when the engaging projection 22 is fit into the engaging groove 13 of the adaptor connecting member 10.

The adaptor connecting member 10 has, at its distal portion, an attaching projected portion 16 which is abutted against the forceps valve 8a at a predetermined position thereof, when the adaptor connecting member 10 is attached to the forceps valve 8a.

A supporting-base portion 10x is externally projected near a distal edge portion of the tube member 11 close to the attaching projected portion 16 onto the outer surface of the tube member 11. A supporting-shaft inserting hole 10a is pierced through the supporting-base portion 10x in the direction perpendicular to the axial direction of the tube member 11. Engaged with the supporting-shaft inserting hole 10a are supporting shafts 32a of a pair of supporting members 32 of the treatment tool position changing member 30, which will be described later, in the sandwiching direction of the supporting-base portion 10x. The treatment tool position changing member 30 is rotatably and coaxially supported to the supporting-base portion 10x.

The treatment tool integrating member 20 is continuously arranged to the adaptor connecting member 10 by using a flexible long member 21, and has the engaging projection 22 for fixing the treatment tool 50 in close contact at a predetermined position by pressing the engaging projection 22 against the engaging groove 13 (refer to FIG. 5) of the adaptor connecting member 10 with a predetermined force and by elastically modifying it.

Specifically, the treatment tool integrating member 20 comprises the flexible long member 21 containing an elastic member such as silicon rubber and a distal portion 23 including the engaging projection 22, which are integrally formed.

One end portion of the flexible long member 21 is engaged in and fixed to a fixing pin 17 arranged to the adaptor connecting member 10 at its predetermined position, thereby continuously arranging the adaptor connecting member 10 and the treatment tool integrating member 20.

The distal portion 23 on the other end side of the flexible long member 21 is planar, and the engaging projection 22 is projected in the direction perpendicular to the planar distal portion 23.

The engaging projection 22 has the same dimension as the internal dimension of the engaging groove 13 of the adaptor connecting member 10, and further has substantially the same shape as that. The engaging projection 22 has, at the distal side thereof, an abutting groove 22a having its cross-section of a predetermined shape (for example, substantially U shape) so as to press the treatment tool 50.

The boss 22b is externally projected at a predetermined position on both side surfaces of the engaging projection 22 in the longitudinal direction. When the engaging groove 13 of the adaptor connecting member 10 is fit into the engaging projection 22 of the treatment tool integrating member 20, the boss 22b is fit into the engaging hole 15 of the adaptor connecting member 10. Thus, the treatment tool integrating member 20 is not pulled-out from the adaptor connecting member 10.

Figure 7:
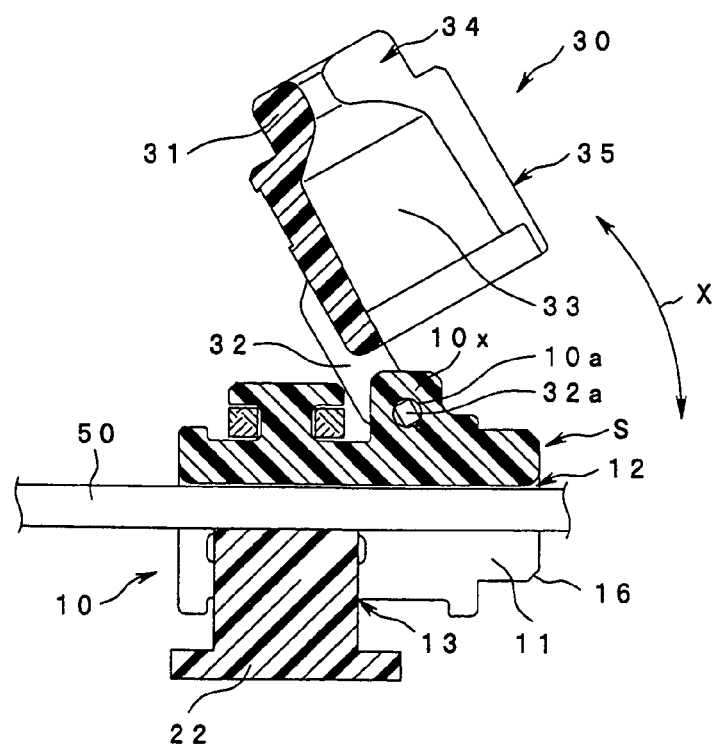
FIG. 7 is a side sectional view showing a state in which the engaging projection of the treatment tool integrating member is fit into the engaging groove of the adaptor connecting member in the adaptor for endoscope forceps opening shown in FIG. 1.

The treatment tool position changing member 30 comprises: a tube member 31 which is rotatably arranged to the adaptor connecting member 10 and mainly contains a resin member; and the pair of supporting members 32 which have their distal portions projected to one end of the tube member 31, coaxially and rotatably support the tube member 31 to the adaptor connecting member 10 in a direction shown by an arrow X in FIG. 7, and connect the tube member 31 to the adaptor connecting member 10.

Referring to FIG. 7, the tube member 31 comprises: a through-groove 33 in which the treatment tool 50 is inserted and detached along the axial direction substantially in the center thereof; and an opening notch portion 35 which is communicated with the through-groove 33.

The tube member 31 has, at the distal portion on the side opposite the arrangement side of the supporting members 32, an attaching projected portion 34 at which the adaptor 9 is detachable to the forceps valve 8a of the endoscope 1.

The supporting shafts 32a are implanted to the pair of supporting members 32 at facing positions near one end portions of the supporting members 32. The supporting shafts 32a are fit into the supporting-shaft inserting hole 10a of the adaptor connecting member 10, thereby rotatably and coaxially support the treatment tool position changing member 30 to the adaptor connecting member 10 and connecting the treatment tool position changing member 30 and the adaptor connecting member 10.

Thus, the treatment tool position changing member 30 is arranged and evacuated between the adaptor connecting member 10 and the forceps opening 8. That is, the treatment tool position changing member 30 is arranged or evacuated between the adaptor connecting member 10 and the forceps opening 8, thereby setting two inserting positions of the distal portion of the treatment tool 50 which is supported by the adaptor 9 and is inserted in the treatment tool channel.

The adaptor 9 according to the first embodiment is used by integrally connecting and combining three members of the adaptor connecting member 10, the treatment tool integrating member 20, and the treatment tool position changing member 30.

In other words, one end of the flexible long member 21 of the treatment tool integrating member 20 is fixed to the fixing pin 17 of the adaptor connecting member 10. Thus, the treatment tool integrating member 20 is connected to the adaptor connecting member 10 via the flexible long member 21.

The supporting shafts 32a of the supporting members 32 of the treatment tool position changing member 30 are engaged with the supporting-shaft inserting holes 10a of the adaptor connecting member 10. Thus, the treatment tool position changing member 30 is rotatably and coaxially supported to the adaptor connecting member 10 in a direction shown by an arrow X in FIG. 7. Simultaneously, the treatment tool position changing member 30 is connected to the adaptor connecting member 10, thereby integrating the three members of the adaptor connecting member 10, the treatment tool integrating member 20, and the treatment tool position changing member 30. In this state, the engaging groove 13, the opening groove 12, and the opening notch portion 35 of the through-groove 33 are arranged substantially on the straight line. Into/from the linearly-formed groove portions, the treatment tool 50 is inserted/detached.

The adaptor 9 according to the first embodiment is used in two state including one state in which the treatment tool position changing member 30 is arranged on the front side of a reference surface S on the distal side of the adaptor connecting member 10 (refer to FIGS. 5 and 7) and another state in which the treatment tool position changing member 30 is not arranged by evacuating treatment tool position changing member 30 from the front surface of the reference surface S on the distal side of the adaptor connecting member 10. That is, the length (dimension) of the adaptor 9 in the axial direction is changed by two steps as the above-mentioned two states.

Figure 10:
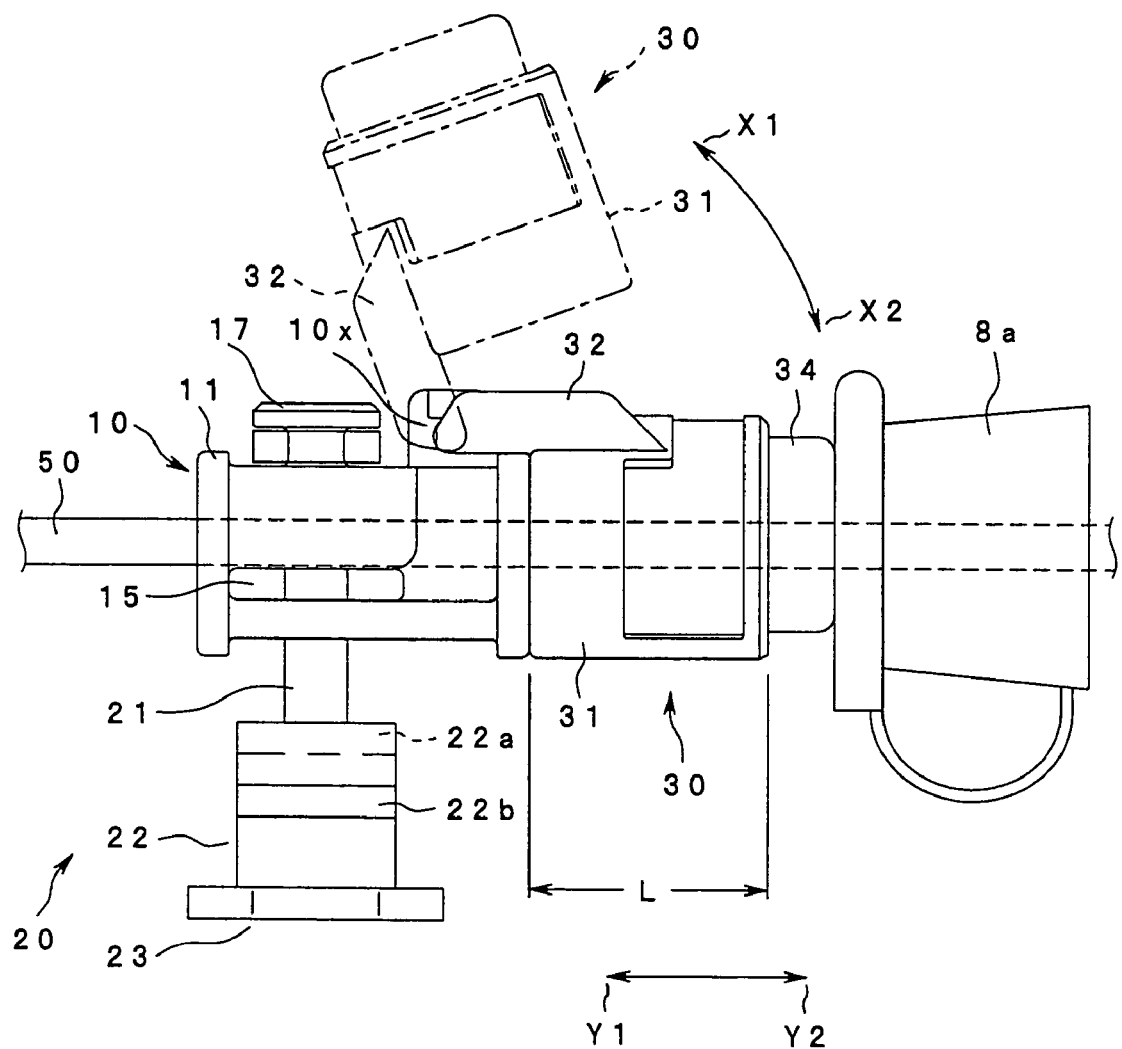
FIG. 10 is a side view showing a state in which the long status adaptor for endoscope forceps opening shown in FIG. 1 is attached to the forceps valve.

That is, when the treatment tool position changing member 30 is arranged in front of the reference surface S on the distal side of the adaptor connecting member 10, namely, changing from the state in which the treatment tool position changing member 30 is arranged to cover the attaching projected portion 16 of the adaptor connecting member 10 (state shown in FIG. 10) to the state in which the treatment tool position changing member 30 is rotated in a direction shown by an arrow X1 in FIG. 10 and the treatment tool position changing member 30 is evacuated from the front side of the reference surface S on the distal side of the adaptor connecting member 10 (state shown by a one-dotted line in FIG. 10 and a state shown in FIG. 8), the length (dimension) of the adaptor 9 in the axial direction is set to be shorter with a length L shown in FIG. 10.

Hereinbelow, a description is given of the operation upon using the adaptor 9 with the foregoing structure according to the first embodiment. In the following, an example is given of using the shape detecting probe as the treatment tool 50 which is inserted in the treatment tool channel of the endoscope 1.

The shape detecting probe as the treatment tool 50 is inserted from the forceps valve 8a of the forceps opening 8 in the endoscope 1. Then, the treatment tool 50 is inserted at the desired position in the treatment tool channel. At the arrangement position, the distal portion of the shape detecting probe is near the inside of the distal portion 2a of the endoscope 1, corresponding to a predetermined position for preventing the projection from the front surface of the distal portion 2a. Further, at the arrangement position, the shape detecting probe is positioned by using an adaptor 9A according to the first embodiment.

Therefore, the shape detecting probe is arranged at the desired position in the treatment tool channel and then the shape detecting probe is attached to the opening groove 12 of the adaptor connecting member 10. After that, the engaging projection 22 of the treatment tool integrating member 20 is pressed to the engaging groove 13 of the adaptor connecting member 10 with predetermined force and is elastically modified, thereby fitting the engaging projection 22 into the engaging groove 13 (state shown in FIG. 6).

When the engaging projection 22 is fit into the engaging groove 13, the engagement of the adaptor connecting member 10 and the treatment tool integrating member 20 is held by fitting the boss 22b of the engaging projection 22 into the engaging hole 15 arranged in the halfway of the engaging groove 13. The treatment tool integrating member 20 is not easily pulled-out from the adaptor connecting member 10. In this state, the shape detecting probe is fixed and held so that it is sandwiched between the abutting groove 22a of the treatment tool integrating member 20 and the bottom of the opening groove 12 of the adaptor connecting member 10. That is, in this state, the shape detecting probe is regulated in the movement in the axial direction so as to prevent the easy movement thereof.

After attaching the adaptor 9 at the desired position of the shape detecting probe, the adaptor 9 is abutted against the forceps valve 8a and is arranged at a predetermined position. Further, the adaptor 9 is integrated with the forceps valve 8a (refer to FIG. 8 or 10).

Figure 8:
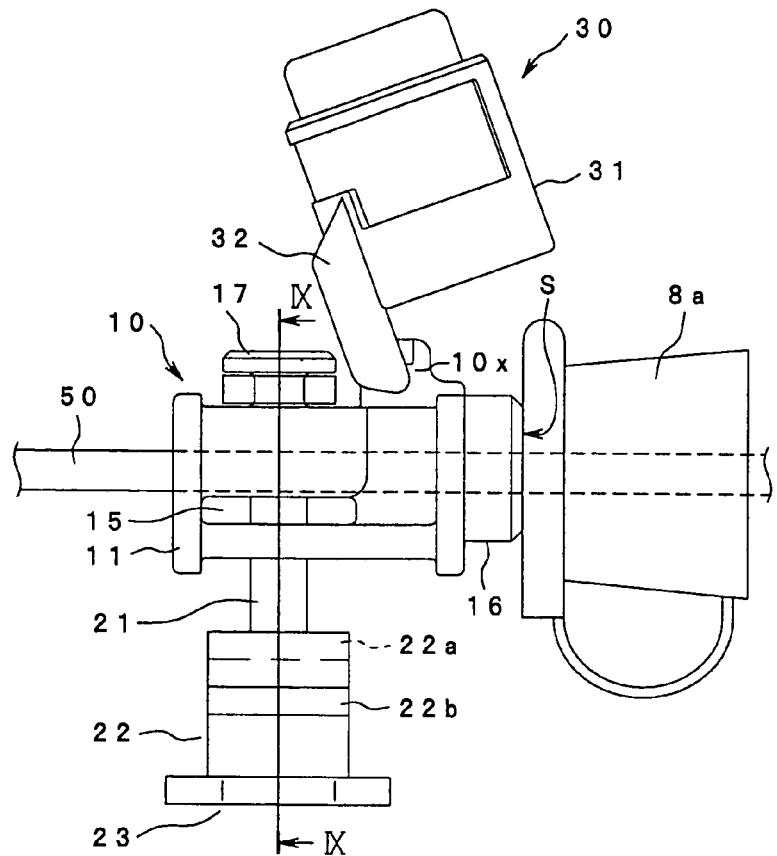
FIG. 8 is a side view showing a state in which the short status adaptor for endoscope forceps opening shown in FIG. 1 is attached to a forceps valve.
Figure 9:
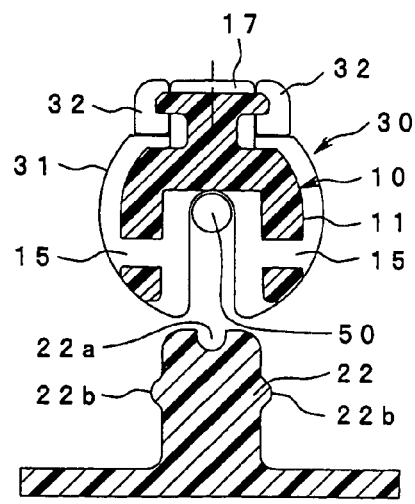
FIG. 9 is a sectional view along a IX-IX line shown in FIG. 8.

When the adaptor 9 is in the state shown in FIG. 8, the attaching projected portion 16 of the adaptor connecting member 10 is abutted against the forceps valve 8a. When the adaptor 9 is in the state shown in FIG. 10, the attaching projected portion 34 of the treatment tool position changing member 30 is abutted against the forceps valve 8a.

When the adaptor 9 is in the state shown in FIG. 10, the adaptor 9 is moved with only the small amount in a direction shown by an arrow Y1 in FIG. 10, then, the attaching projected portion 34 is detached from the forceps valve 8a, and the treatment tool position changing member 30 is rotated in a direction shown by an arrow X1 in FIG. 10. In this state, the attaching projected portion 16 of the adaptor connecting member 10 is abutted against the forceps valve 8a by moving the adaptor 9 in a direction shown by an arrow Y2 in FIG. 10 and, then, the state is as shown in FIG. 8. By doing so, the shape detecting probe is set to a state in which it advances in the inserting direction with the length L shown in FIG. 10.

In this state, when the adaptor 9 is moved in the direction shown by the arrow Y1 in FIG. 10, the shape detecting probe is moved in the pull-out direction. On the contrary, when the adaptor 9 is moved in the direction shown by the arrow Y2 in FIG. 10, the shape detecting probe is moved in the inserting direction. Since the shape detecting probe is positioned by the adaptor 9, the shape detecting probe is not inserted in front of the predetermined position.

Further, the change from the state in FIG. 8 (state shown by the one-dotted line in FIG. 10) to the state in FIG. 10, the adaptor 9 is moved with the small amount in the direction shown by the arrow Y1 in FIG. 10. After that, the attaching projected portion 16 is detached from the forceps valve 8a, and the treatment tool position changing member 30 is rotated in a direction shown by an arrow X2 in FIG. 10. Thus, the treatment tool position changing member 30 is arranged to the attaching projected portion 16 of the adaptor connecting member 10. In this state, the adaptor 9 is moved in a direction shown by the arrow Y2 in FIG. 10, then, the attaching projected portion 34 of the treatment tool position changing member 30 is abutted against to the forceps valve 8a, and the state shown in FIG. 10 is obtained. By doing so, the shape detecting probe is evacuated in the pull-out direction with the length L shown in FIG. 10.

The shape detecting probe is positioned and fixed to the treatment tool channel of the endoscope 1 by using the adaptor 9, and the inserting portion 2 of the endoscope 1 is inserted from the anus, for example, to the body cavity.

In this case, even when the inserting portion 2 is twisted or the bending portion 2b is bent, the adaptor 9 holds the shape detecting probe, thereby positioning the shape detecting probe at a predetermined point. Therefore, the operator is able to concentrate himself/herself on the inserting operation.

On the other hand, when, like biopsy forceps, the treatment tool 50 inserted in the treatment tool channel is projected from the distal end surface of the endoscope 1 with the predetermined amount if necessary, the adaptor 9 is used in the state shown in FIG. 8, namely, in the state in which the attaching projected portion 34 of the treatment tool position changing member 30 is abutted against the forceps valve 8a.

In this case, the adaptor 9 is attached to the treatment tool 50 and the treatment tool 50 is inserted to a predetermined position of the treatment tool channel. After that, the engaging projection 22 of the treatment tool integrating member 20 is pressed in the engaging groove 13 of the adaptor connecting member 10 in the above-mentioned sequence. Thus, the adaptor 9 fixes and holds the treatment tool 50 at the predetermined position in the treatment tool channel.

Next, the inserting portion 2 of the endoscope 1 is inserted to the body cavity from the oral cavity, for example. Then, the distal surface of the endoscope 1 faces a desired observed portion with a predetermined interval. In this state, the attaching projected portion 34 is detached from the forceps valve 8a if necessary. The treatment tool position changing member 30 is rotated and then is detached from the front surface of the adaptor connecting member 10.

Thereafter, the attaching projected portion 16 of the adaptor connecting member 10 is abutted against the forceps valve 8a (state shown in FIG. 8). Thus, the distal portion of the biopsy forceps as the treatment tool 50 fixed and held by the adaptor 9 is moved forward with the length L shown in FIG. 10 and the distal portion of the biopsy forceps is projected with a predetermined amount from the distal surface of the endoscope 1. In this state, the abnormal organ in the body cavity is removed.

By setting the length L of the treatment tool position changing member 30, the return amount or projecting amount of the treatment tool is arbitrarily set.

As mentioned above, according to the first embodiment, the adaptor 9 is abutted against the forceps valve 8a of the forceps opening 8 in the endoscope 1, and the adaptor 9 fixes and holds the treatment tool 50 which is inserted in the treatment tool channel from the forceps opening 8. Then, the adaptor 9 is structured by integrating the adaptor connecting member 10, the treatment tool integrating member 20, and the treatment tool position changing member 30. As a consequence, the components are not fallen or are not lost during the use of the endoscope 1.

Further, when the adaptor 9 is attached to the treatment tool 50 at the desired position by only the single operation for pressing the engaging projection 22 of the treatment tool integrating member 20 into the engaging groove 13 of the adaptor connecting member 10. The adaptor 9 is easily attached to the treatment tool 50.

Furthermore, the opening groove 12 and the engaging groove 13 are provided for the adaptor connecting member 10, and the through-groove 33 is further provided for the treatment tool position changing member 30. Therefore, the adaptor 9 is easily detached from the treatment tool 50. In particular, after inserting the treatment tool 50 in the treatment tool channel, the adaptor 9 is easily attached.

In addition, the adaptor 9 fixes and holds the treatment tool 50 which is inserted in the treatment tool channel and thus the movement of the treatment tool 50 is regulated in the treatment tool channel. The treatment tool 50 is certainly positioned in the treatment tool channel. Therefore, when the treatment tool 50 is arranged in the treatment tool channel and the inserting portion 2 of the endoscope 1 is operated on the hand side, the operator concentrates himself on the operation of the inserting portion 2 in the endoscope 1 on the hand side without paying attention to the holding state of the treatment tool 50.

It is possible to easily set the above-mentioned two states of the one state in which the treatment tool position changing member 30 is arranged on the front side of the adaptor connecting member 10 forming the adaptor 9 and the other state in which the treatment tool position changing member 30 is evacuated therefrom. Therefore, the treatment tool 50 is easily projected or returned.

According to the first embodiment, the treatment tool position changing member 30 is rotatably arranged to the adaptor connecting member 10. Further, a plurality of treatment tool position changing members are provided with different lengths L and they overlaid and are combined, the return amount or projecting amount of the treatment tool 50 can arbitrarily be changed in a plurality of steps.

In this case, the plurality of treatment tool position changing members with different lengths L are attached with a string member, or the like, for example, at a predetermined position of the adaptor connecting member 10. Then, the adaptor 9 can be structured by properly and arbitrarily combining the treatment tool position changing members. Therefore, the return amount or projecting amount of the treatment tool 50 can easily and arbitrarily be changed or be adjusted in the plurality of steps.

Hereinbelow, a description is given of an adaptor for endoscope forceps opening according to the second embodiment of the present invention.

Figure 11:
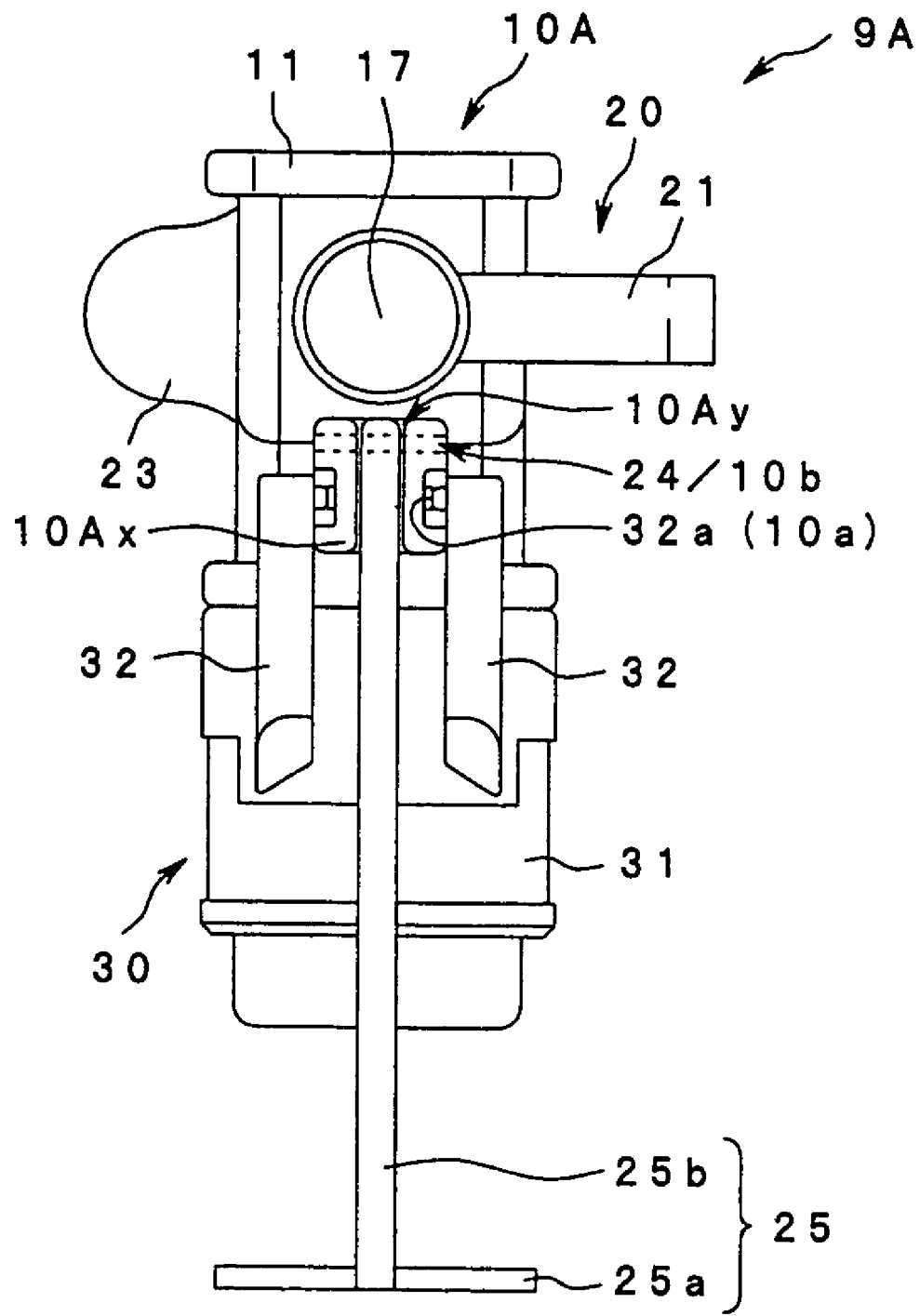
FIG. 11 is a front plan view showing the structure of an adaptor for endoscope forceps opening according to a second embodiment of the present invention.
Figure 12:
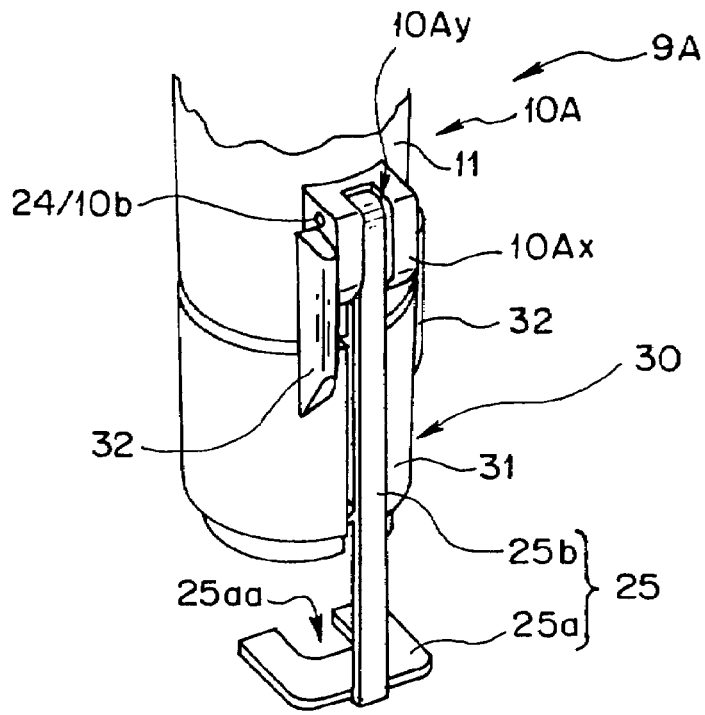
FIG. 12 is an enlarged perspective view of a main portion mainly showing a guide member and its attaching portion in the adaptor for endoscope forceps opening shown in FIG. 11.
Figure 13:
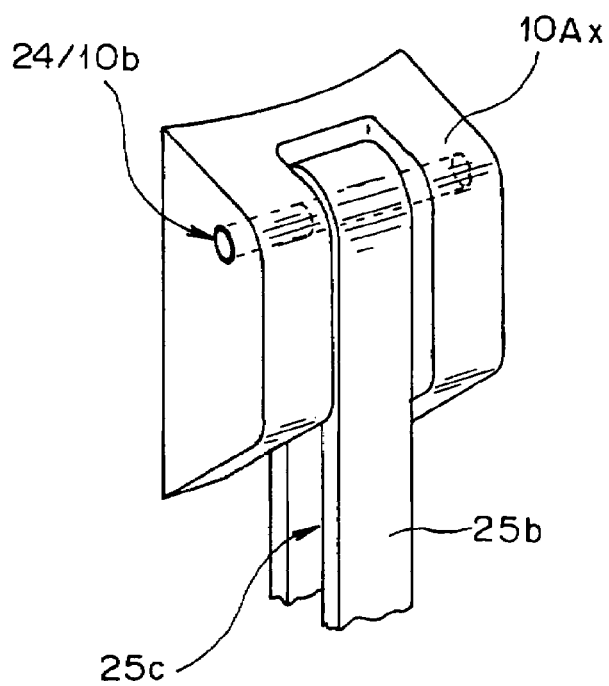
FIG. 13 is an enlarged perspective view of a main portion showing a further enlarged part of the structure shown in FIG. 12.
Figure 14:
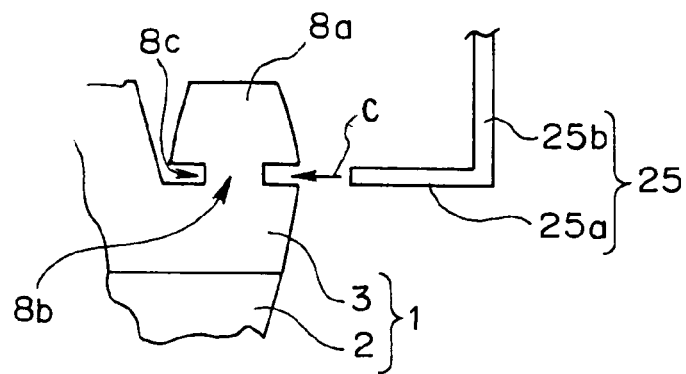
FIG. 14 is an enlarged view of a main portion showing only an adjacent portion of a forceps valve having the arrangement of the adaptor for endoscope forceps opening shown in FIG. 11.

Referring to FIGS. 11 to 13, the structure of an adaptor 9A for endoscope forceps opening (hereinafter, abbreviated to an adaptor, similarly to the first embodiment) is substantially the same as that of the adaptor 9 according to the first embodiment. However, unlike the adaptor 9, the adaptor 9A further comprises a guide member which guides the adaptor 9A so as to certainly abut the adaptor 9A against the forceps valve 8a of the forceps opening 8 in the endoscope 1. Therefore, the same reference numerals as those according to the first embodiment denote the same components, a description thereof is omitted, and only different components are described later.

According to the second embodiment, the adaptor 9A holds the treatment tool at a predetermined position of the treatment tool channel, similarly to the first embodiment, and regulates the movement of the treatment tool. The adaptor 9A mainly comprises: an adaptor connecting member 10A; the treatment tool integrating member 20; and the treatment tool position changing member 30. The adaptor connecting member 10A, the treatment tool integrating member 20, and the treatment tool position changing member 30 are integrally arranged.

Among the adaptor connecting member 10A, the treatment tool integrating member 20, and the treatment tool position changing member 30, which form the adaptor 9A, the treatment tool integrating member 20 and the treatment tool position changing member 30 are the same as those according to the first embodiment.

Further, among the adaptor connecting member 10A, the treatment tool integrating member 20, and the treatment tool position changing member 30, which form the adaptor 9A, referring to FIG. 11, the adaptor connecting member 10A mainly comprises: a tube member 11 containing the resin member; the opening groove 12 formed in the same direction as the axial direction of the treatment tool or the like which needs to be inserted or detached in/from the tube member 11 (not shown, refer to FIGS. 6 and 7 according to the first embodiment); the engaging groove 13 which is integrally formed to the opening groove 12; and the supporting-shaft inserting hole 10a for coaxially and rotatably supporting the treatment tool position changing member 30. The adaptor connecting member 10A is detachably arranged to the forceps valve 8a of the forceps opening 8 in the endoscope 1, which is communicated with the treatment tool channel in which the treatment tool 50 is inserted.

A supporting-base portion 10Ax is externally projected near a distal edge portion of the tube member 11 close to the attaching projected portion 16 onto the outer surface of the tube member 11. Similarly to the first embodiment, the supporting-shaft inserting hole 10a is pierced through the supporting-base portion 10Ax in the direction perpendicular to the axial direction of the tube member 11. In addition, according to the second embodiment, a guide-member supporting shaft inserting hole 10b is pierced through the supporting-base portion 10Ax. A guide-member supporting shaft 24 rotatably, slidably, and coaxially supports a guide member 25 within a predetermined range (which will be described later), and integrally and continuously arranges the guide member 25 and the adaptor connecting member 10A. Further, the guide-member supporting shaft 24 is inserted in the guide-member supporting shaft inserting hole 10b.

A U-shaped groove 10Ay having the substantially U-shaped cross-section is formed substantially in the center of the supporting-base portion 10Ax. The U-shaped groove 10Ay is formed along the axial direction of the tube member 11, and is pierced from one end portion of the supporting-base portion 10Ax to the other end portion. The groove of the U-shaped groove 10Ay has a guide shaft portion 25b of the guide member 25 which is slidable therein.

The guide member 25 comprises: a fixing plate portion 25a containing a steel plate or the like; and the guide shaft portion 25b having one end which is fixed to one side edge portion of the fixing plate portion 25a.

The fixing plate portion 25a comprises a U-shaped notch portion 25aa having an opening at one end thereof. The notch portion 25aa is engaged at a predetermined position near the forceps opening 8 in the endoscope 1. Specifically, the notch portion 25aa is sandwiched between the peripheral distal portion of the forceps opening 8 and the base portion of the forceps valve 8a arranged to the forceps opening 8 in the endoscope 1. Corresponding to the specific structure of the notch portion 25aa, a predetermined peripheral groove 8c is formed at a base portion 8b of the forceps valve 8a. The U-shaped notch portion 25aa of the fixing plate portion 25a is detachably formed to the peripheral groove 8c, and therefore is engaged. When the notch portion 25aa is attached to the peripheral groove 8c, the structure is obtained as shown by a solid line in FIG. 15. The dimension of the inner width of the notch portion 25aa is set so that it is equal to the diameter of the base portion 8b of the forceps valve 8a or is slightly larger. The dimension of thickness of the notch portion 25aa is set so that it is substantially equal to the width dimension of the peripheral groove 8c or slightly smaller (thinner). Therefore, when the notch portion 25aa is attached to the base portion 8b of the forceps valve 8a, the guide member 25 is not easily fallen from the periphery of the forceps opening 8. Meanwhile, only by pressing the notch portion 25aa to the base portion 8b of the forceps valve 8a, the guide member 25 is arranged at a predetermined position. When the guide member 25 is taken out, only the pull-out operation of the guide member 25 is sufficient. Therefore, the guide member 25 is detachably arranged to the forceps valve 8a.

One end of the guide shaft portion 25b is fixed at one side edge portion of the fixing plate portion 25a, namely, one side edge portion on the opposite side of the forming side of the opening of the notch portion 25aa so that the guide shaft portion 25b stands on the plane of the fixing plate portion 25a.

As mentioned above, the one end of the guide shaft portion 25b is integrally fixed to the one side edge portion of the fixing plate portion 25a. A sliding portion 25c is circularly formed at the range from another end of the guide shaft portion 25b to the middle position thereof. The guide-member supporting shaft 24 is inserted in the sliding portion 25c. The guide-member supporting shaft 24 is inserted in the guide-member supporting shaft inserting hole 10b of the supporting base member 10Ax, and both ends of the guide-member supporting shaft 24 are coaxially supported to the supporting base member 10Ax.

Figure 15:
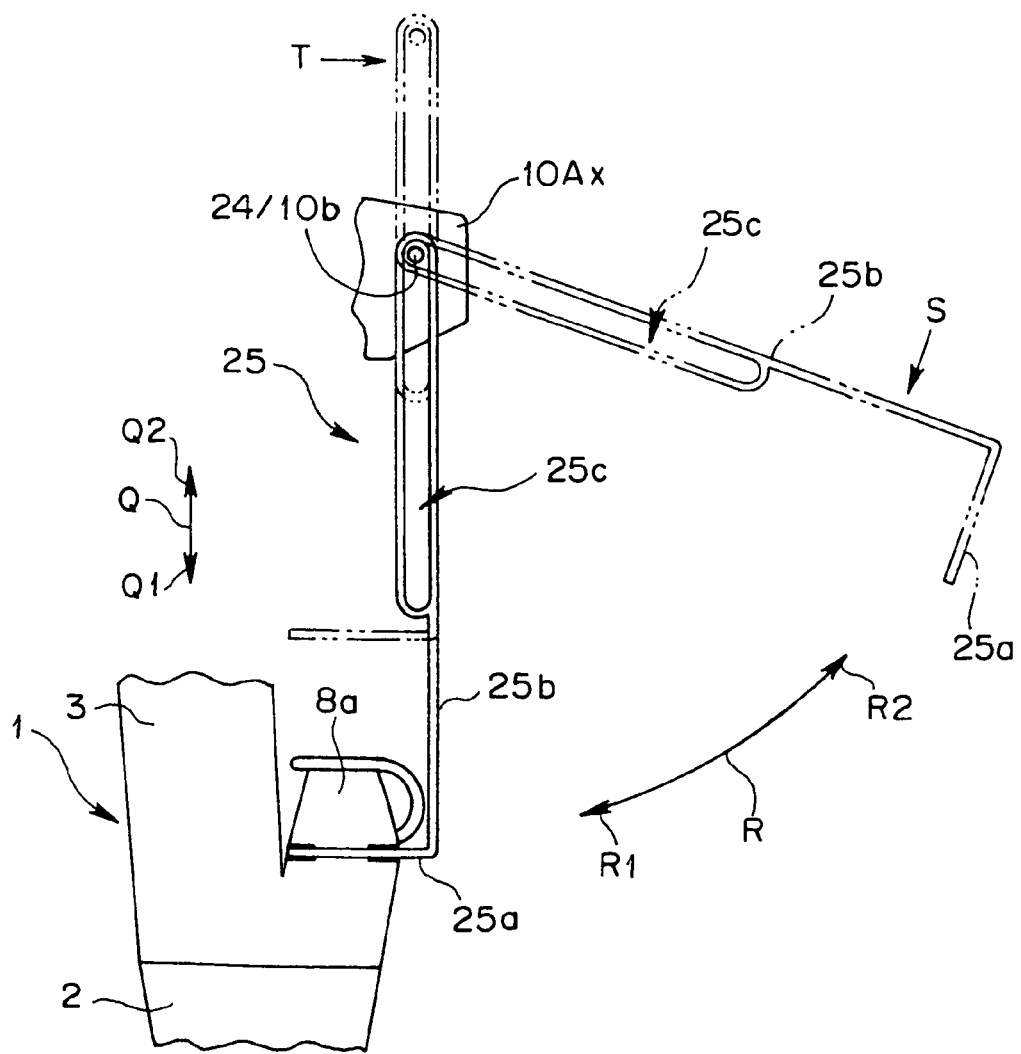
FIG. 15 is a diagram explaining the operation of the guide member in the adaptor for endoscope forceps opening shown in FIG. 11.

That is, the guide-member supporting shaft 24 coaxially and rotatably supports the guide member 25 (in a direction shown by an arrow R in FIG. 15). Further, the guide-member supporting shaft 24 slidably and coaxially supports the guide member 25 within a predetermined range in a direction shown by an arrow Q in FIG. 15. Furthermore, the guide-member supporting shaft 24 integrally and continuously arranges the guide member 25 and the adaptor connecting member 10A.

Other structures are the same as those according to the first embodiment.

The adaptor 9A according to the second embodiment is used by integrally connecting and combining four components of the adaptor connecting member 10A, the treatment tool integrating member 20, the treatment tool position changing member 30, and the guide member 25.

Hereinbelow, a description is given of the operation upon using the adaptor 9A with the above-mentioned structure according to the second embodiment. In the following, similarly to the first embodiment, the treatment tool 50 inserted in the treatment tool channel of the endoscope 1 uses, e.g., a shape detecting probe.

The shape detecting probe as the treatment tool 50 is inserted from the forceps valve 8a of the forceps opening 8 in the endoscope 1. The treatment tool 50 or the like is arranged at a desired position in the treatment tool channel. At the desired position, the distal portion of the shape detecting probe is near the inside of the distal portion 2a of the endoscope 1 and is not projected from the front surface of the distal portion 2a. At the position, the shape detecting probe is positioned by using the adaptor 9A according to the second embodiment, similarly to the first embodiment.

Therefore, the shape detecting probe is arranged at the desired position in the treatment tool channel, and is attached at the position on the straight-line arrangement of the engaging groove 13 and the opening groove 12 of the adaptor connecting member 10A and the opening notch portion 35 of the through-groove 33 of the treatment tool position changing member 30. In this case, the guide member 25 is at a position S of the fixing plate portion 25a shown by a dotted line in FIG. 15, namely, at a position where the fixing plate portion 25a is evacuated from the axial direction of the adaptor 9A. Further, the guide member 25 is at a position T of the guide shaft portion 25*b* shown by a dotted line in FIG. 15, namely, at an arbitrary position within a predetermined range for moving the guide shaft portion 25*b* in the axial direction of the adaptor 9A.

In this state, the guide member 25 is rotated in a direction shown by an arrow R1 in FIG. 15 and is slid in a direction shown by an arrow Q1 in FIG. 15. Then, the notch portion 25*aa* of the fixing plate portion 25*a* is fit into the peripheral groove 8*c* of the base portion 8*b* of the forceps valve 8*a* of the forceps opening 8 in the endoscope 1, and is at the position shown by a solid line in FIG. 15. In this state, the guide-member supporting shaft 24 is at the terminal end portion in the circular portion of the sliding portion 25*c*. Thus, the guide member 25 is fixed to the forceps opening 8 in the endoscope 1. The adaptor 9A continuously arranged to the guide member 25 is abutted against the forceps valve 8*a*.

Figure 6:
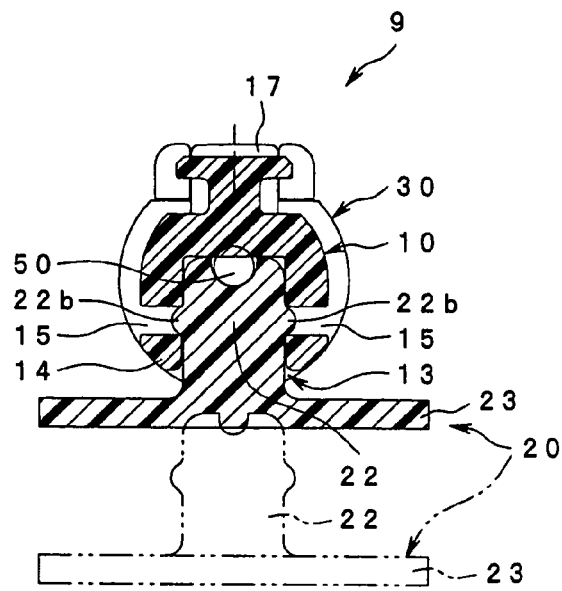
FIG. 6 is a longitudinal sectional view showing a fitting portion at which an engaging projection of a treatment tool integrating member is fit into an engaging groove of the adaptor connecting member in the adaptor for endoscope forceps opening, when the adaptor for endoscope forceps opening shown in FIG. 1 is attached to the treatment tool.

After that, the engaging projection 22 of the treatment tool integrating member 20 is pressed with a predetermined force to the engaging groove 13 in the adaptor connecting member 10A, thus is elastically modified, and is fit into it (state shown in FIG. 6). Thus, the adaptor 9A is at the predetermined position of the shape detecting probe. At this time point, the movement of the shape detecting probe is regulated for the endoscope 1 so as to prevent the easy movement in the invading direction in the treatment tool channel.

The adaptor 9A is moved in a direction shown by an arrow Q2 in FIG. 15 and then the adaptor 9A is moved in the direction for pulling-out the shape detecting probe. On the other hand, the adaptor 9A is moved in the direction shown by the arrow Q1 in FIG. 15 and, then, the adaptor 9A is moved in the direction for inserting the shape detecting probe. In this case, the shape detecting probe is positioned to the adaptor 9A and therefore is not inserted in front side of the predetermined position.

On the other hand, like the biopsy forceps, when the treatment tool 50 inserted in the treatment tool channel is projected with a predetermined amount from the distal surface of the endoscope 1 if necessary, the adaptor 9A is used by abutting the attaching projected portion 34 of the treatment tool position changing member 30 against the forceps valve 8*a*, as mentioned above.

In this case, the attaching projected portion 34 is detached from the forceps valve 8*a* if necessary, the treatment tool position changing member 30 is rotated, and the treatment tool position changing member 30 is detached from the front surface of the adaptor connecting member 10A. After that, the attaching projected portion 16 of the adaptor connecting member 10A is abutted against the forceps valve 8*a*. In this case, the adaptor 9A is stable in the axial direction and moves along the guide member 25.

Then, the distal portion of the treatment tool 50 fixed and held by the adaptor 9A is moved forward with a predetermined dimension (refer to the length L shown in FIG. 10). The distal portion of the treatment tool 50 is projected from the distal surface of the endoscope 1 with the predetermined amount.

Upon detaching the adaptor 9A, the engaging projection 22 of the treatment tool integrating member 20 fit into the engaging groove 13 of the adaptor connecting member 10 is pulled-out with the predetermined force. After that, the fixing plate portion 25*a* of the guide member 25 is pulled-out from the peripheral groove 8*c* of the forceps valve 8*a*. Then, the guide member 25 is rotated in a direction shown by an arrow R2 in FIG. 15. Then, the shape detecting probe or the treatment tool 50 such as the biopsy forceps is detached from the groove portion of the adaptor 9A.

As mentioned above, according to the second embodiment, the same advantages as those according to the first embodiment are obtained. In addition, the guide member 25 is integrally formed to the adaptor 9A. Thus, when the adaptor 9A is moved in the axial direction for the positioning operation after attaching the adaptor 9A to the treatment tool 50 or the like, the adaptor 9A is moved along the guide member 25 in the axial direction and therefore the adaptor 9A is stably moved.

Next, a description is given of an adaptor for endoscope forceps opening according to third embodiment of the present invention.

Figure 16:
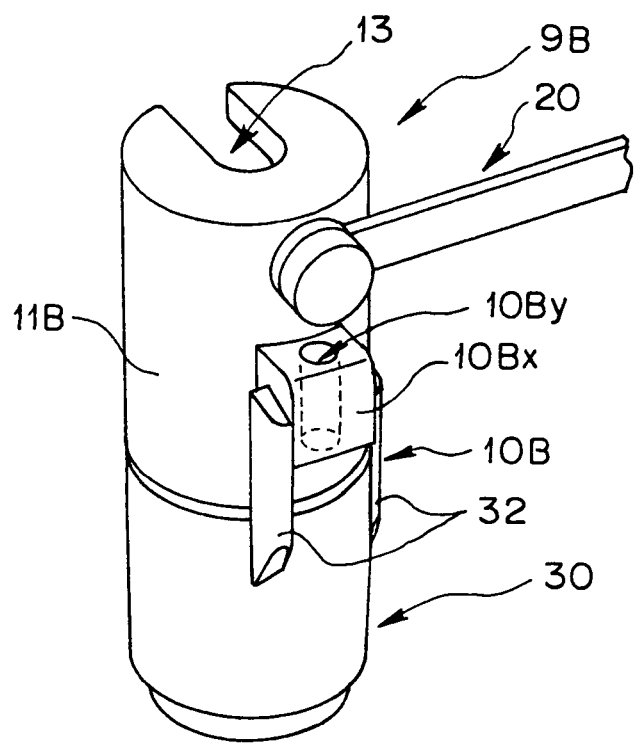
FIG. 16 is a perspective view showing the structure of an adaptor for endoscope forceps opening according to a third embodiment of the present invention.
Figure 17:
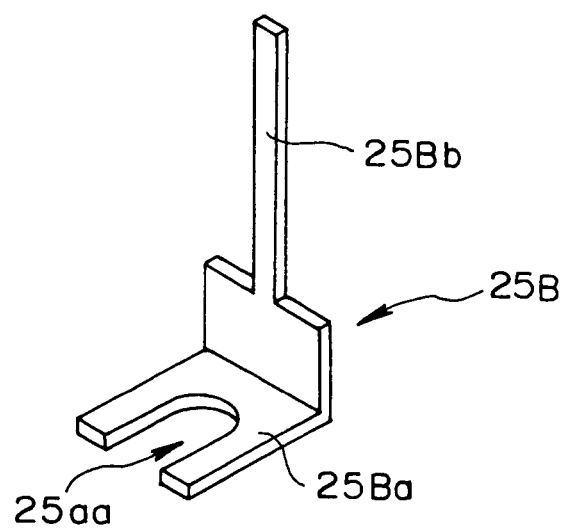
FIG. 17 is a perspective view showing a guide member which is used together with the adaptor for endoscope forceps opening show in FIG. 16.
Figure 18:
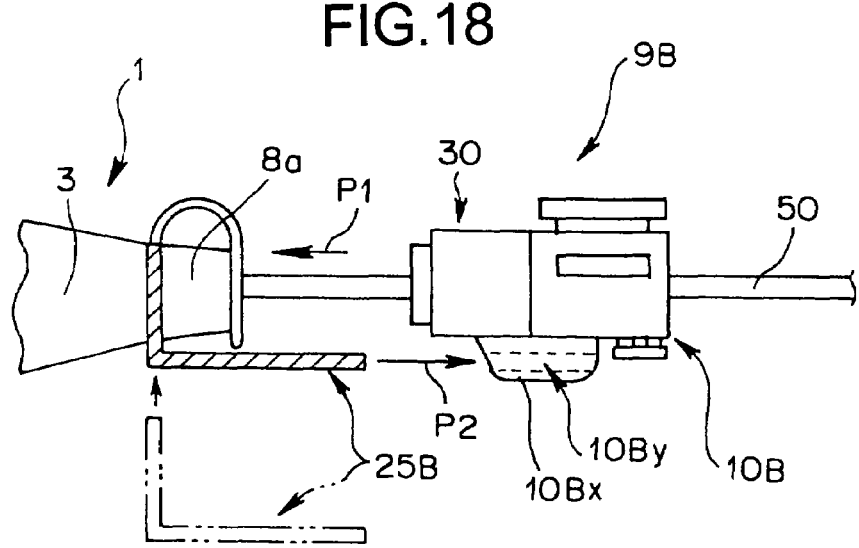
FIG. 18 is a diagram explaining the operation upon using the adaptor for endoscope forceps opening shown in FIG. 16 and the guide member shown in FIG. 17.

As shown in FIGS. 16 to 18, an adaptor 9B for endoscope forceps opening (hereinafter, abbreviated to an adaptor, similarly to the first and second embodiments) according to the third embodiment has the same structure as that of the adaptor 9A according to the second embodiment. However, according to the third embodiment, the adaptor 9B and a guide member 25B are separately arranged. The same reference numerals as those according to the second embodiment denote the same components, a description thereof is omitted, and only different components are described later.

According to the third embodiment, the adaptor 9B holds the treatment tool at a predetermined position of the treatment tool channel, similarly to the second embodiment, and regulates the movement of the treatment tool. Referring to FIG. 16, the adaptor 9B mainly comprises: an adaptor connecting member 10B; the treatment tool integrating member 20; and the treatment tool position changing member 30. The adaptor connecting member 10B, the treatment tool integrating member 20, and the treatment tool position changing member 30 and the like are integrally and continuously arranged.

Among the adaptor connecting member 10B, the treatment tool integrating member 20, and the treatment tool position changing member 30, which form the adaptor 9B, the treatment tool integrating member 20 and the treatment tool position changing member 30 are the same as those according to the first and second embodiments.

Further, among the adaptor connecting member 10B, the treatment tool integrating member 20, and the treatment tool position changing member 30, which form the adaptor 9B, referring to FIG. 16, the adaptor connecting member 10B has the structure of a supporting-base portion 10Bx, unlike the second embodiment (refer to FIG. 11).

The supporting-base portion 10Bx mainly contains a resin member, and is formed at a predetermined position on the peripheral surface of a tube member 11B having the opening groove 12, the engaging groove 13, and the supporting-shaft inserting hole 10*a*. A guide hole 10By pierced through the supporting-base portion 10Bx is formed substantially in the center of the inside of the supporting-base portion 10Bx. The guide hole 10By is formed along the axial direction of the tube member 11B, and is pierced through a portion from one end distal portion to another distal portion of the supporting-base portion 10Bx. A guide shaft portion 25Bb of the guide member 25B is slidably engaged with the guide hole 10By.

On the other hand, referring to FIG. 17, the guide member 25B according to the third embodiment is a member in place of the guide member 25A according to the second embodiment. That is, the guide member 25B comprises: a fixing plate portion 25Ba containing a steel plate and having a U-shaped notch portion 25*aa* with an opening at one end thereof; and the guide shaft portion 25Bb as a shaft-shaped member which is extended in the direction perpendicular to the plane of the fixing plate portion 25Ba from one side edge portion of the fixing plate portion 25Ba and is quadrangular.

The guide shaft portion 25Bb is inserted in the guide hole 10By of the adaptor 9B upon using the adaptor 9B as mentioned above. Thus, the guide shaft portion 25Bb has a function for guiding the movement of the adaptor 9B in the axial direction.

Other structures are the same as those according to the second embodiment.

The adaptor 9B according to the third embodiment is used by integrally connecting and combining the three components of the adaptor connecting member 10B, the treatment tool integrating member 20, and the treatment tool position changing member 30. In addition, the movement of the adaptor 9B is guided by the guide member 25B.

Hereinbelow, a description is given of the operation upon using the adaptor 9B with the above-mentioned structure according to the third embodiment. In the following, similarly to the first embodiment, the treatment tool 50 inserted in the treatment tool channel of the endoscope 1 uses, e.g., a shape detecting probe.

First, the guide member 25B is fixed to the forceps opening 8 of the endoscope 1. That is, the notch portion 25aa of the fixing plate portion 25a in the guide member 25B is fit into the peripheral groove 8c of the base portion 8b of the forceps valve 8a of the forceps opening 8 in the endoscope 1 (state shown by a solid line in FIG. 18 changed from the state shown by a dotted line).

Next, the treatment tool 50 (shape detecting probe) is inserted from the forceps valve 8a of the forceps opening 8 in the endoscope 1. The treatment tool 50 is arranged at the desired position in the treatment tool channel. In this state, the adaptor 9B is attached at a predetermined position of the shape detecting probe. That is, the shape detecting probe is attached at the straight-line arrangement position of the engaging groove 13 and the opening groove 12 of the adaptor connecting member 10B and the opening notch portion 35 of the through-groove 33 in the treatment tool position changing member 30.

The adaptor 9B is moved near the forceps opening 8 in accordance with the shape detecting probe (in a direction shown by an arrow P1 in FIG. 18). Simultaneously, the guide shaft portion 25Bb of the guide member 25B is inserted in the guide hole 10By of the adaptor 9B, and the adaptor 9B is moved (in a direction shown by an arrow P2 in FIG. 18).

When the adaptor 9B is abutted against the forceps valve 8a, the engaging projection 22 of the treatment tool integrating member 20 is fit into the engaging groove 13 of the adaptor connecting member 10B. Thus, the adaptor 9B is positioned at the predetermined position of the shape detecting probe. At this time point, the movement of the shape detecting probe is regulated so as to prevent the easy movement in the invading direction of the treatment tool channel (direction shown by an arrow P in FIG. 18) in the endoscope 1.

From the state, the adaptor 9B is moved along the direction shown by the arrow P2 in FIG. 18 and then the shape detecting probe is moved in the direction for pulling-out the shape detecting probe. Referring to FIG. 18, the guide shaft portion 25Bb is moved to the position for completely pulling-out the guide shaft portion 25Bb out of the guide hole 10By. Then, the treatment tool position changing member 30 is rotated in the predetermined direction as mentioned above according to the first embodiment, and the treatment tool position changing member 30 is evacuated from the shaft of the shape detecting probe. The adaptor 9B is moved in the direction shown by the arrow P1 in FIG. 18. The attaching projected portion 16 of the adaptor connecting member 10B is abutted against the forceps valve 8a. In this state, upon moving the adaptor 9B, the guide shaft portion 25Bb is inserted in the guide hole 10By and thus the adaptor 9B is moved along the guide shaft portion 25Bb in the axial direction. Therefore, the adaptor 9B is always moved in the predetermined axial direction with stability. As mentioned above, the shape detecting probe is set to advance in the inserting direction with a predetermined length (refer to the length L in FIG. 10).

Other operations are the same as those according to the second embodiment.

According to the third embodiment, the same advantages as those according to the second embodiment are obtained. In addition, the guide member 25B according to the third embodiment is arranged independently of the adaptor 9B. The guide shaft portion 25Bb of the guide member 25B is provided with varied dimension or shape depending on the application and then it can easily be used in accordance with the application.

Figure 19:
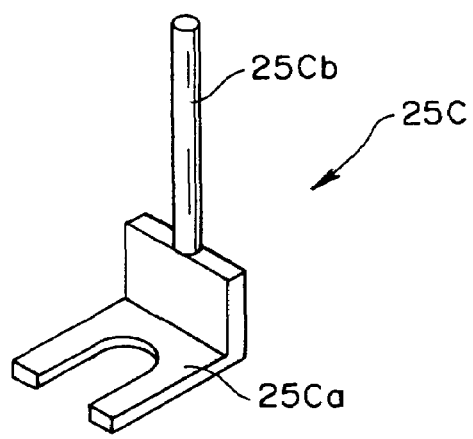
FIG. 19 is a perspective view showing a guide member in an adaptor for endoscope forceps opening according to one modification of the third embodiment of the present invention.

FIG. 19 is a perspective view showing a guide member of an adaptor for endoscope forceps opening according to one modification of the third embodiment. Referring to FIG. 19, a guide member 25C comprises: a fixing plate portion 25Ca with substantially the same shape of the fixing plate portion 25Ba according to third embodiment; and a guide shaft portion 25Cb which is integrally formed to the fixing plate portion 25Ca and has substantially the circular- or elliptical-shaped cross-section.

Figure 20:
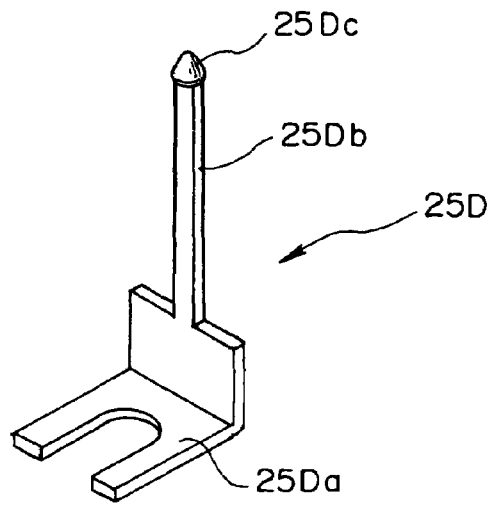
FIG. 20 is a perspective view showing a guide member in an adaptor for endoscope forceps opening according to another modification of the third embodiment of the present invention.

FIG. 20 is a perspective view showing a guide member of an adaptor for endoscope forceps opening according to another modification of the third embodiment. Referring to FIG. 20, a guide member 25D comprises: a fixing plate portion 25Da with substantially the same shape of the fixing plate portion 25Ba according to third embodiment; and a guide shaft portion 25Db which is integrally formed to the fixing plate portion 25Da and has substantially the rectangular-shaped (although not shown, substantially circular- or elliptical-shaped) cross-section. The distal portion of the guide shaft portion 25Db has a distal member 25Dc having the cross-sectional area slightly wider than that of the cross-sectional area substantially equal to or slightly wider than that of the guide hole 10By. In this case, the distal member 25Dc comprises an elastic member.

Therefore, upon inserting the guide shaft portion 25Db in the guide hole 10By, the distal member 25Dc invades from one side (forceps valve 8a side) and is not pulled-out to the other side, and then the adaptor for endoscope forceps opening is not fallen.

The material of the guide member according to the second and third embodiments and the two modifications of the third embodiment may be rigid or may contain an elastic member with the restoring property such as plate spring or the like.

It should be understood that the present invention is not limited to those embodiments and various changes and modifications thereof could be made without departing from the spirit of scope of the invention as defined in the appended claims.

What is claimed is:

1. An adaptor for endoscope forceps opening comprising:
   an adaptor connecting member which is detachably arranged to a forceps valve of an endoscope forceps opening communicated with a treatment tool inserting channel for inserting a treatment tool;
   a treatment tool integrating member which is fixed in close contact at a part of the treatment tool projected from the forceps valve; and a treatment tool position changing member which stepwise changes the inserting position of the treatment tool in the treatment tool inserting channel when the treatment tool integrating member is in close contact at the treatment tool, wherein the adaptor connecting member comprises an opening groove which is formed in its axial direction and from/to which the treatment tool is detached/attached, and an engaging groove which is integrally formed to the opening groove, the treatment tool integrating member comprises a flexible long member which is connected to the adaptor connecting member and an engaging projection which is fit into the engaging groove and fixes the treatment tool in close contact therewith, the treatment tool position changing member is rotatably connected to the adaptor connecting member and comprises a through-groove from which the treatment tool is detached and an opening notch portion communicated with the through-groove, and the opening groove, the engaging groove, the through-groove, and the opening notch portion are arranged substantially on the straight line.

2. An adaptor for endoscope forceps opening according to claim 1, wherein the adaptor for endoscope forceps opening is arranged or evacuated between the adaptor connecting member and the forceps valve, thus to stepwise setting the inserting position in the treatment tool inserting channel of the treatment tool when the treatment tool integrating member is in contact with the treatment tool.

3. An adaptor for endoscope forceps opening according to claim 1, wherein the adaptor connecting member rotatably and integrally connects the flexible long member to the treatment tool integrating member.

4. An adaptor for endoscope forceps opening according to claim 1, wherein the treatment tool is fixed to a predetermined position in close contact by pressing the engaging projection with a predetermined force, elastically modifying it, and fitting it to the engaging groove, when the engaging projection of the treatment tool integrating member is engaged with the engaging groove of the adaptor connecting member.

5. An adaptor for endoscope forceps opening according to claim 1, further comprising:

a guide member which guides the movement in the axial direction.

6. An adaptor for endoscope forceps opening according to claim 5, wherein the guide member is rotatably arranged to the adaptor connecting member and further is slidably arranged in the axial direction, and is integrally connected to the adaptor connecting member.

7. An adaptor for endoscope forceps opening according to claim 5, wherein the guide member is detachably formed to the forceps valve of the endoscope forceps opening.

8. An adaptor for endoscope forceps opening according to claim 5, wherein the guide member is arranged independent of the adaptor connecting member.

* * * * *